(12) United States Patent
Pomeroy

(10) Patent No.: US 12,097,133 B2
(45) Date of Patent: Sep. 24, 2024

(54) MECHANICAL JOINT WITH SWITCHABLE, ROTATION-CONSTRAINING CLUTCH

(71) Applicant: Paul Pomeroy, Auburn, WA (US)

(72) Inventor: Paul Pomeroy, Auburn, WA (US)

(*) Notice: Subject to any disclaimer, the term of this patent is extended or adjusted under 35 U.S.C. 154(b) by 636 days.

(21) Appl. No.: 17/322,112

(22) Filed: May 17, 2021

(65) Prior Publication Data

US 2021/0267776 A1 Sep. 2, 2021

Related U.S. Application Data

(63) Continuation of application No. 15/769,603, filed as application No. PCT/US2016/058948 on Oct. 26, 2016, now Pat. No. 11,020,247.

(Continued)

(51) Int. Cl.
| | |
|---|---|
| A61F 2/64 | (2006.01) |
| A61F 2/50 | (2006.01) |
| A61F 2/60 | (2006.01) |
| A61F 2/68 | (2006.01) |
| A61F 2/76 | (2006.01) |
| A61F 5/01 | (2006.01) |
| F16D 23/12 | (2006.01) |
| F16D 41/08 | (2006.01) |
| F16D 41/20 | (2006.01) |
| F16D 47/04 | (2006.01) |

(52) U.S. Cl.
CPC .................. *A61F 2/64* (2013.01); *A61F 2/76* (2013.01); *A61F 5/0102* (2013.01); *F16D 41/08* (2013.01); *F16D 41/206* (2013.01); *F16D 47/04* (2013.01); *A61F 2002/5039* (2013.01); *A61F 2002/5043* (2013.01); *A61F 2002/5073* (2013.01); *A61F 2002/607* (2013.01); *A61F 2002/608* (2013.01); *A61F 2002/6845* (2013.01); *F16D 2023/123* (2013.01)

(58) Field of Classification Search
CPC ........ F16D 41/08; F16D 41/206; F16D 41/20; F16D 13/30; F16D 13/36; F16D 13/50; F16D 13/56; F16D 2023/123
See application file for complete search history.

(56) References Cited

U.S. PATENT DOCUMENTS 2,863,684 A * 12/1958 Carroll ................. A61F 2/6607
623/47
2,870,453 A * 1/1959 Vasquez ................. A61F 2/604
623/43

(Continued)

FOREIGN PATENT DOCUMENTS

WO WO-2007108551 A1 * 9/2007 ........... A61F 5/0102

*Primary Examiner* — Jonathan P Masinick
(74) *Attorney, Agent, or Firm* — OPWII, LLC

(57) ABSTRACT

The current document is directed to a two-way, by-passable, overrunning clutch incorporated within a mechanical prosthetic knee that provides functionality similar to a biological knee or incorporated in another articulated device, such as a robotic or orthotic articulated device or member. The currently disclosed two-way, by-passable, overrunning clutch allows for two-way free rotation when disabled, but, when enabled, prevents rotation in one direction while allowing free rotation in the other direction. In the mechanical prosthetic knee, the two-way, by-passable, overrunning clutch is enabled by application of a mechanical force and disabled by removal of the mechanical force.

15 Claims, 11 Drawing Sheets

Related U.S. Application Data

(60) Provisional application No. 62/246,485, filed on Oct. 26, 2015.

(56) References Cited

U.S. PATENT DOCUMENTS

| | | | | |
|---|---|---|---|---|
| 2,943,622 | A | * | 7/1960 | Nelson .................. A61F 5/0125 623/44 |
| 3,361,235 | A | * | 1/1968 | Sacchini ................... F16B 1/04 192/223.4 |
| 4,191,283 | A | * | 3/1980 | Keeny, III ............ F16D 27/105 192/22 |
| 4,451,939 | A | * | 6/1984 | Thompson ................ A61F 2/64 623/44 |
| 4,760,903 | A | * | 8/1988 | Stegelmeier .......... F16D 13/025 192/81 C |
| 6,139,586 | A | * | 10/2000 | Wagner ..................... A61F 2/68 623/44 |
| 6,500,138 | B1 | * | 12/2002 | Irby ...................... F16D 41/206 623/44 |
| 8,764,850 | B2 | * | 7/2014 | Hansen ..................... A61F 2/70 623/47 |
| 2002/0143344 | A1 | * | 10/2002 | Taylor .................... A61B 17/66 606/105 |
| 2014/0074255 | A1 | * | 3/2014 | Starker ..................... A61F 2/68 623/50 |

\* cited by examiner

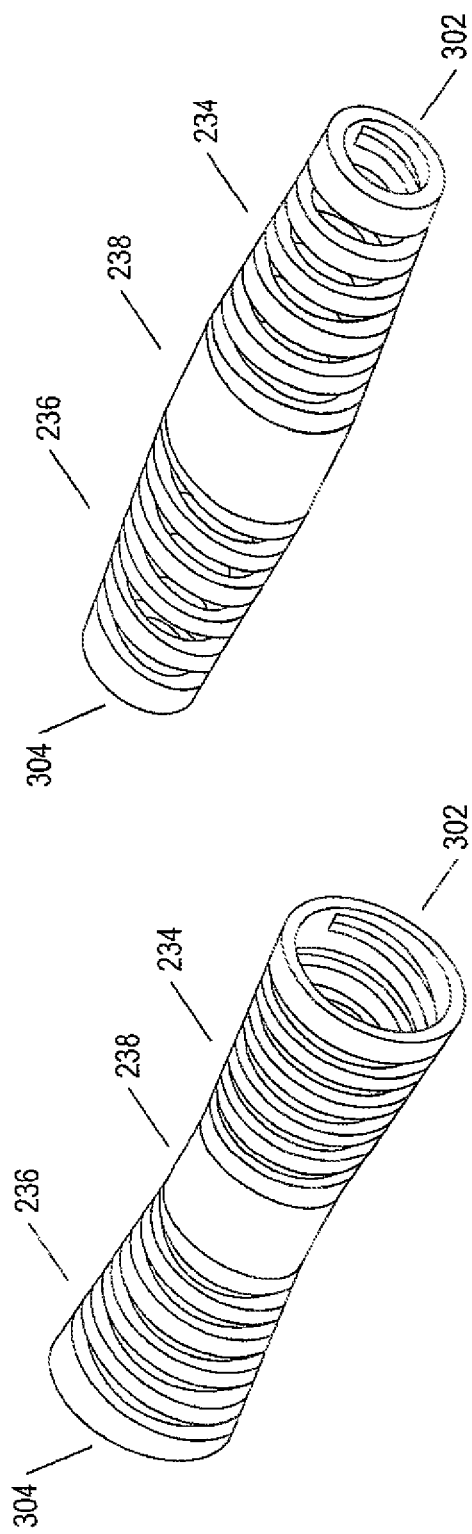
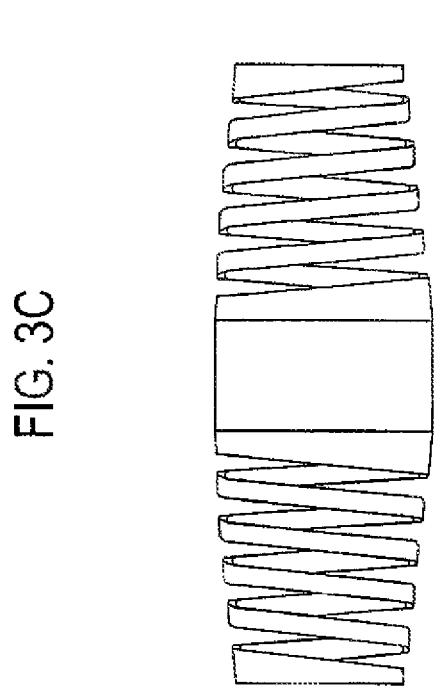
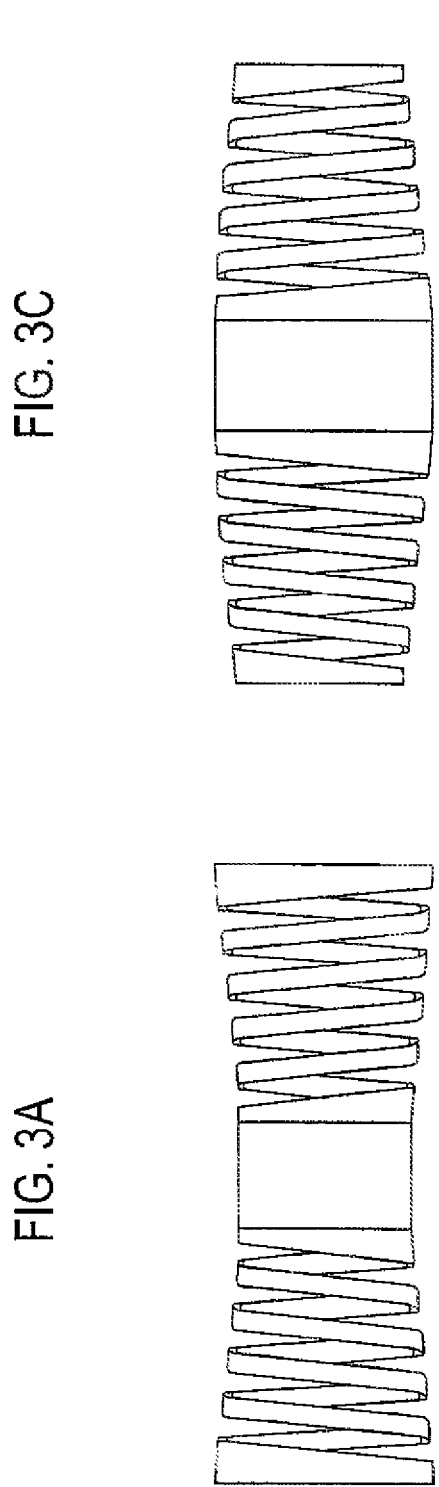
FIG. 3C
FIG. 3D
FIG. 3A
FIG. 3B

MECHANICAL JOINT WITH SWITCHABLE, ROTATION-CONSTRAINING CLUTCH

CROSS-REFERENCE TO RELATED APPLICATIONS

This application claims priority to U.S. Pat. No. 11,020, 247, issued Jun. 1, 2021, U.S. application Ser. No. 15/769, 603, filed Apr. 19, 2018, which claims priority to PCT Application No. PCT/US2016/058948, filed Oct. 26, 2016, which claims the benefit of Provisional Application No. 62/246,485, filed Oct. 26, 2015.

TECHNICAL FIELD

The present disclosure is directed to artificial joints used in prosthetic, exoskeletal, orthotic, and/or robotic devices, and, in particular, to a two-way, by-passable, overrunning clutch that is incorporated into prosthetic joints to provide for a switchable constraint to rotation.

BACKGROUND

The design and manufacturing of prosthetic limbs and joints is a large and important industry. Prosthetics are used to address limb-loss injuries from military conflicts, transportation accidents, and many different types of diseases and pathologies, including a currently rising incidence of diabetes. Currently, large design and development efforts are directed towards sophisticated electromechanical prosthetics controlled by one or more microprocessors, with some designs directed to at least partially controlling motion and operation of a prosthetic limb through sensing and responding to nervous activity within a patients' bodies. Many of these complex and expensive prosthetics provide simulated natural motion and biological-limb-like operational characteristics, but they are associated with many disadvantages. A first disadvantage is cost. For many people, even in developed countries, an artificial limb costing many tens of thousands of dollars to hundreds of thousands of dollars is beyond reach. In many developing countries, including poorer countries wracked by military conflicts and residual dangers, such as land mines and undetected unexploded bombs, modern, sophisticated electromechanical prosthetics are far too expensive even for relatively wealthy inhabitants. The sophisticated electromechanical prosthetics also have significant shortcomings, including difficulties in providing reliable power sources, steep learning curves, physical-fitness requirements, and training overheads associated with use of such prosthetics, many types of failure modes that generally accompany complex designs and implementations, including lack of water resistance and vulnerability to damaging environmental agents, and frequent maintenance and repair overheads. For these reasons, there remains great interest in developing new mechanical prosthetics that are simple to manufacture, relatively inexpensive, robust, and reliable.

SUMMARY

The current document is directed to a two-way, by-passable, overrunning clutch incorporated within a mechanical prosthetic knee that provides functionality similar to a biological knee or incorporated in another articulated device, such as a robotic or orthotic articulated device or member. The currently disclosed two-way, by-passable, overrunning clutch allows for two-way free rotation when disabled, but, when enabled, prevents rotation in one direction while allowing free rotation in the other direction. In the mechanical prosthetic knee, the two-way, by-passable, overrunning clutch is enabled by application of a mechanical force and disabled by removal of the mechanical force.

BRIEF DESCRIPTION OF THE DRAWINGS

FIGS. 3A-D exaggeratingly illustrate the clutching operation of the dual-wrap-spring clutch element.

DETAILED DESCRIPTION

Figure 1:
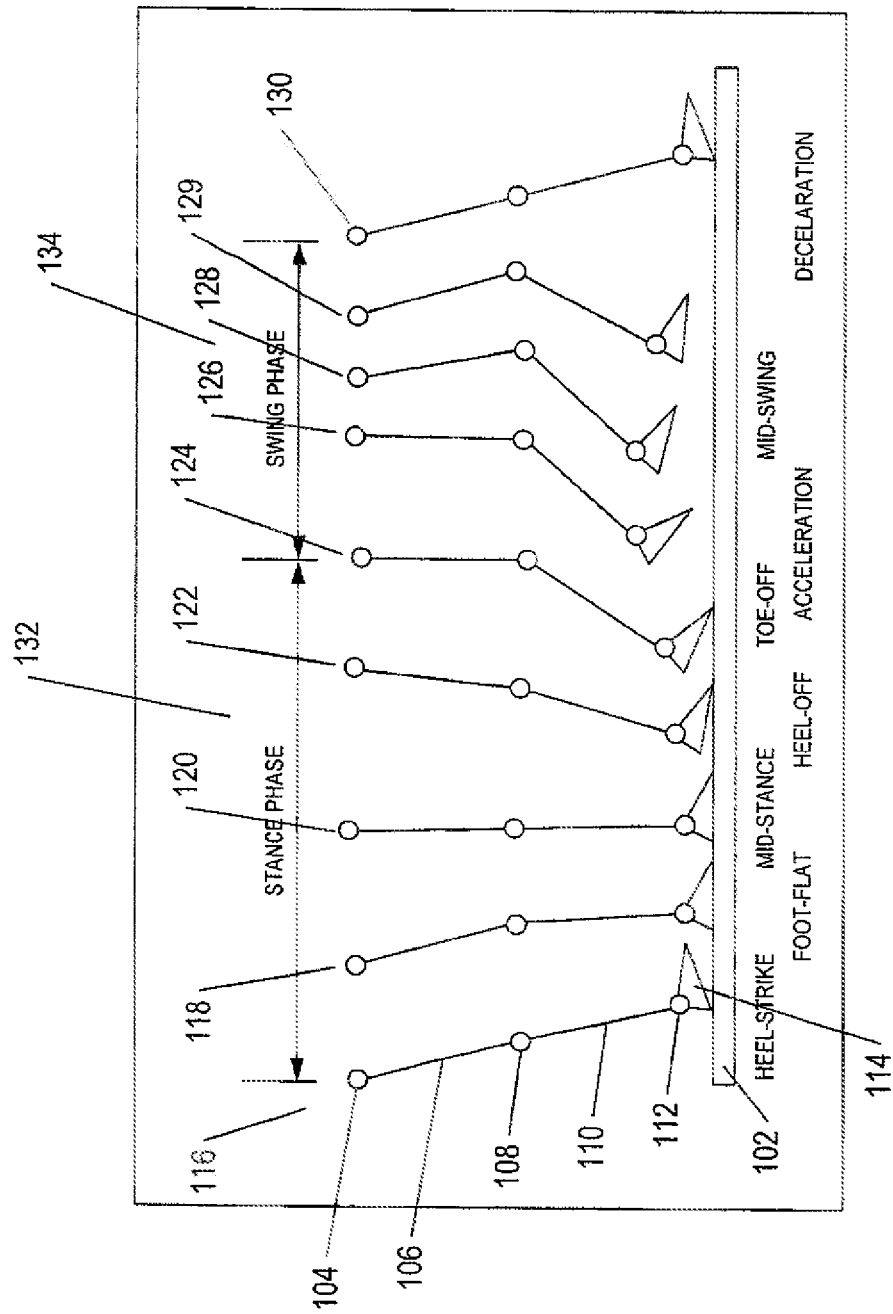
FIG. 1 illustrates the human gait cycle.

FIG. 1 illustrates the human gait cycle. FIG. 1 shows the gait cycle for the right leg of a person walking forward, in a left-to-right direction, along a horizontal surface 102. In FIG. 1, the right leg is abstractly represented by a rotating hip joint 104, an upper-leg shaft 106, a rotating knee joint 108, a lower-leg shaft 110, a rotating ankle joint 112, and a foot 114. In the first position 116 shown in FIG. 1, the leg has been thrust forward, during walking, with the heel of the foot 114 just making contact with the horizontal surface 102. As the person continues walking in the forward direction, the person is propelled forward largely by exertion of muscles in the other leg along with a forward shift in the person's center of mass, with the knee joint rotating to allow the person's body to travel forward while the foot remains securely positioned, by friction, on the horizontal surface. This is illustrated in the second position 118 shown in FIG. 1. In position 120, the person's body has moved further forward, straightening the leg. In position 122, the knee joint continues to rotate, allowing the center of mass of the person's body to continue forward, past the foot and knee. Rotation of the knee joint continues further to position 124, where the ankle joint and knee joint both rotate to allow the person's heel to rise above the horizontal surface and to allow muscle force of the leg to propel the person forward. In position 126, the person's left leg is moving from position 116 to 118, allowing the displayed right leg to become unweighted and the foot to be raised to a position in which it does not contact the horizontal surface. This allows the knee to rotate in an opposite direction, in positions 128-130 so that the lower leg swings forward in order to make contact with the ground. Note that position 130 is equivalent to position 116, completing the gait cycle.

The gait cycle can thus be described generally as having a stance phase 132 and a swing phase 134. In the stance phase, the knee joint needs to allow the lower leg to rotate in clockwise direction, from the perspective of FIG. 1, in order to straighten from position 118 to position 120. However, the knee must resist rotation in a counter-clockwise direction to prevent the leg from buckling, due to the center of mass of the person's body being located behind the position of the knee, and a resulting fall. By contrast, during the swing phase 134, the knee continues to allow rotation of the lower leg in the clockwise direction but then allows the lower leg to rotate in the counter-clockwise direction in order to facilitate thrusting of the leg forward to begin a next stance phase. In general, during the stance phase, the leg is weighted due to the gravitational force of the person's body pushing down through the leg structure while, in the swing phase 134, the leg is unweighted.

For transfemoral amputees, a prosthetic knee joint is generally used to permit walking and other types of locomotion and movement. Prosthetic knees generally attempt to provide rotational constraints during the stance phase, to prevent buckling of the knee, while allowing the knee to swing relatively freely during the swing phase. While a certain level of rotational constraints during the swing phase may be overcome by an amputee by altering the gait cycle, such as a modified gait cycle referred to as "peg-leg walking," failure of a prosthetic knee to provide for only one-way rotation during the stance phase would render the prosthetic knee unsuitable and dangerous.

As discussed above, prosthetic knees can be broadly classified as either microprocessor-controlled, electromechanical prosthetic knees, or as purely mechanical knees without microprocessors and generally without digital electronics. Various different types of mechanical knees use hydraulics, pneumatics, friction braking, and/or geometrical interferences of linkages in order to prevent unconstrained knee rotation when the leg is weighted, in the stance phase. Electromechanical knees may use similar mechanical components, but generally employ software-controlled microprocessors and other digital-electronic components to control operation of the prosthetic knee.

In the case of conventional, currently available mechanical knees, the amputee learns to control the knee with his/her remaining muscles and execute certain techniques during gait to engage knee stability during stance. Unless the user puts the knee in the correct position, the knee is unstable. This takes a great deal of training and expertise and imposes an extra mental workload on the amputee, which, in turn, means more attention and energy expended during walking. Nevertheless, conventional mechanical knees remain widely used because they are generally more durable and less expensive than microprocessor knees.

Microprocessor-controlled knees, on the other hand, monitor various sensors, determine a user's position in the gait cycle, and automatically control engagement of stability control for the user. In fact, such knees remain in stability mode most of the time. This results in greater efficiency in gait and decreased mental workload. However, microprocessor-controlled knees are significantly more expensive, require a power source (typically a battery), and often involve significant tuning and maintenance to function properly.

The current document discloses a new mechanical prosthetic-knee joint that provides the desired constraints on the relative rotation of the lower leg and upper leg when the leg is weighted, during the stance phase, but also provides relatively free rotation of the lower leg with respect to the upper leg, in both directions, when the leg is unweighted during the swing phase. The currently disclosed mechanical prosthetic knee joint is, in a described implementation, a fully mechanical, non-microprocessor-based knee prosthetic. However, in alternative implementations, electronics and control logic, including either or both of state machines and microprocessors, can be incorporated into a prosthetic mechanical knee joint that employs the mechanical components of the currently disclosed mechanical prosthetic knee. In other words, while the currently disclosed mechanical prosthetic knee is adequate for purely mechanical implementations, the currently disclosed mechanical components may additionally be used in more complex, electromechanical prosthetic knees.

Figure 2:
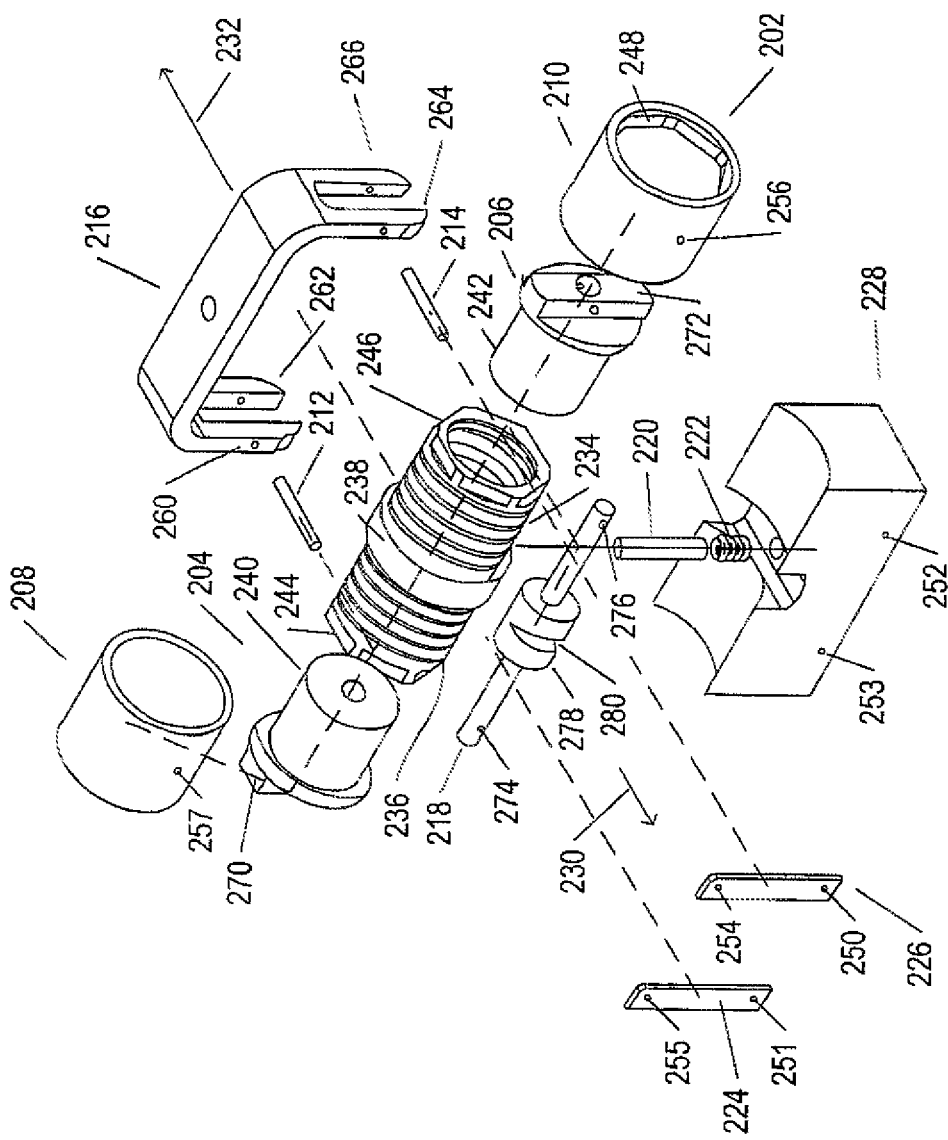
FIG. 2 provides an exploded diagram of the currently disclosed two-way, by-passable, overrunning mechanical clutch that includes a dual-wrap-spring clutch element and that is incorporated in mechanical prosthetic knee joint.

The mechanical constrained-rotation mechanism used in the currently disclosed prosthetic knee is a type of two-way, by-passable, overrunning mechanical clutch. This mechanical clutch is based on a single-piece, dual-wrap-spring clutch element ("WSC"). FIG. 2 provides an exploded diagram of the currently disclosed two-way, by-passable, overrunning mechanical clutch that includes a dual-wrap-spring clutch element and that is incorporated in mechanical prosthetic knee joint. As shown in FIG. 2, the mechanical prosthetic knee joint includes the WSC 202, two arbors 204 and 206, two arbor sleeves 208 and 210, two clutch pins 212 and 214, a yoke 216, a cam-like force adjustor and dimensional constraint 218, a torque transmission pin 220, a torque-transmission-pin spring 222, two flexible linkages 224 and 226, and a lower-leg block 228.

In FIG. 2, were the mechanical prosthetic knee to include a kneecap, it would be facing outward in the direction of arrow 230. The back of the knee would be facing in the direction of arrow 232. The lower-leg block 228 is rigidly affixed to a lower-prosthetic leg assembly, and torque-transmission pin 220 rotationally couples the lower-leg block 228 to the WSC, while the yoke 216 and arbors 204 and 206 are rigidly affixed to an upper-prosthetic-leg assembly. The WSC 202 rotates, along with the torque-transmission pin 220 and lower-leg block 228, relative to the arbors 204 and 206 and yoke 216. The two-way by-passable overrunning clutch mechanism operates to prevent rotation of the lower-leg block 228 and torque-transmission pin 220 in a counter-clockwise direction (in the perspective of a viewer looking into the figure) with respect to the yoke 216 and arbors 204 and 206 when the leg is weighted, in the stance phase, but allows rotation of the lower-leg block 228 and torque-transmission pin in the clockwise direction. In the swing phase, when the leg is unweighted, the lower-leg block 228 and torque-transmission pin 220 can freely rotate in both the counter-clockwise and clockwise directions with respect to the yoke 216 and arbors 204 and 206.

The WSC provides friction-based clutching. The WSC 202 includes two outward-spiraling helical coils 234 and 236 with flattened coils that provide a cylindrical surface complementary to the arbor shafts, discussed below. When the lower-leg block 228 and torque-transmission pin 220, which is affixed through an aperture in a lower portion of the WSC central band 238, rotates outward in the direction of arrow 230, in a clockwise direction with respect to the yoke 216 and arbors 204 and 206, the outward-spiraling coils rotate freely over the surface of the cylindrical arbor shafts 240 and 242. As the WSC rotates with respect to arbors 204 and 206, the outward-spiraling helices appear to be traveling horizontally inwards, towards the central WSC band 238, like the threads of a screw. However, when the lower-leg block 228 and torque-transmission pin 220 are pushed from the front backward, in the direction of arrow 232, in an attempt to rotate the lower-leg block 228 and torque-transmission pin 220 in a counter-clockwise direction with respect to the yoke 216 and arbors 204 and 206, the outwardly spiraling helices 234 and 236 compress down tightly against the surface of the arbor shafts 240 and 242, preventing rotation. Were these outwardly spiraling helices able to rotate along with the lower-leg block and torque-transmission pin in the counter-clockwise direction, the helices would appear to travel outward, in the horizontal direction, towards the distal ends of the arbors 204 and 206.

The arbor sleeves 208 and 210 fit over the arbors 204 and 206 in order to ride above the outwardly spiraling helices of the WSC, with hexagonal nut-like ends 244 and 246 of the WSC mating within complementary hexagonal end fittings 248 of the arbor sleeves 208 and 210. Flexible linkages 224 and 226 are affixed to the lower-leg block 228 via pins through apertures 250-253 and are affixed, via apertures 254-257, to arbor sleeves 208 and 210. When the leg is weighted, the yoke 216, arbor sleeves 208 and 210, arbors 204 and 206, and WSC 202 are forced downward, against torque-transmission pin spring 222 towards the lower-leg block 228. This downward translation of the yoke 216, arbor sleeves 208 and 210, and arbors 204 and 206 result in an upward force transmitted through flexible linkages 234 and 226 to the arbor sleeves 210 and 208, causing the arbor sleeves to rotate in a clockwise direction with respect to arbors 206 and 204 and yoke 216. This rotates the ends of the WSC 244 and 246 in a clockwise direction which may tighten the outwardly spiraling helices against the arbor shafts 240 and 242, allowing the clutching action and preventing rotation of the lower-leg block 228 and torque-transmission pin 220 in a counter-clockwise direction with respect to the yoke 216 and arbors 204 and 206. When the leg is unweighted, the torque-transmission-pin spring 222 pushes the WSC 220 upward with respect to the lower-leg block, resulting in a downward force applied by the flexible linkages 224 and 226 to the arbor sleeves 208 and 210. This results in a counter-clockwise rotation of the arbor sleeves with respect to the arbor 204 and yoke 216, which applies a counter-clockwise rotation to the outwardly spiraling WSC helices 234 and 236, resulting in expanding the diameter of the outwardly spiraling helix cylinders and allowing the helical cylinders to rotate with respect to the arbor shafts.

The tines 260, 262, 264, and 266, two on each side of yoke 216, fit down over the vertical end bars 270 and 272 of the arbors 204 and 206 in the completed assembly, and are affixed to the arbors via clutch pins 212 and 214, which also pass through apertures 274 and 276 at the ends of the cam-like force adjustor and dimensional constraint 218. The cam-like force adjustor and dimensional constraint therefore holds the arbors at a fixed horizontal distance from one another, to resist outward pressure from the outwardly-spiraling helical coils 234 and 236. In addition, the cylindrical cam 278 includes a partial shaft aperture 280 within which the torque-transmission pin slides. As the prosthetic knee joint straightens, additional frictional force is applied by the cam-like force adjustor and dimensional constraint to the torque-transmission pin which, in turn, increases the effect of weight applied to the leg in enabling the two-way, by-passable overrunning clutch mechanism. In a sitting position, an amputee can overcome the clutch operation more readily than in a standing position, allowing for transition from the sitting position to the standing position.

The two-way, by-passable, overrunning mechanical clutch is mechanically symmetrical and fault tolerant. A single wrap spring could, upon mechanical failure, lead to accidents. By using two wrap springs, a single-coil failure does not result in failure of rotational constraint, but is noticeable to an amputee, alerting the amputee that repair is needed. Furthermore, the dual-wrap-spring configuration provides symmetrical distribution of loading forces through the two-way, by-passable, overrunning mechanical clutch, relieving unbalanced stress and potential failure modes.

FIGS. 3A-D exaggeratingly illustrate the clutching operation of the dual-wrap-spring clutch element. FIGS. 3A-B show the WSC in an open, disengaged configuration. In this configuration, the diameter of the flattened, outwardly spiraling helical coils 234 and 236 increases from the central WSC band 238 outward towards ends 302 and 304. FIG. 3B provides a different perspective of the disengaged WSC clutch configuration. As discussed above, when the leg is weighted, the flexible linkages (224 and 226 in FIG. 2) impart a clockwise rotation to the arbor sleeves 208 and 210, tightening the helical coils of the WSC against the arbor shafts, as exaggeratingly shown in FIGS. 3C and 3D. The diameter of the outwardly spiraling helical coils 234 and 236 decreases from the central WSC band 238 towards the ends 302 and 304. FIG. 3D shows the tightened helical coils from a different perspective. However, in actual operation, the changes in diameter along the lengths of the outwardly spiraling helical coils of the WSC are visually imperceptible.

Figure 4:
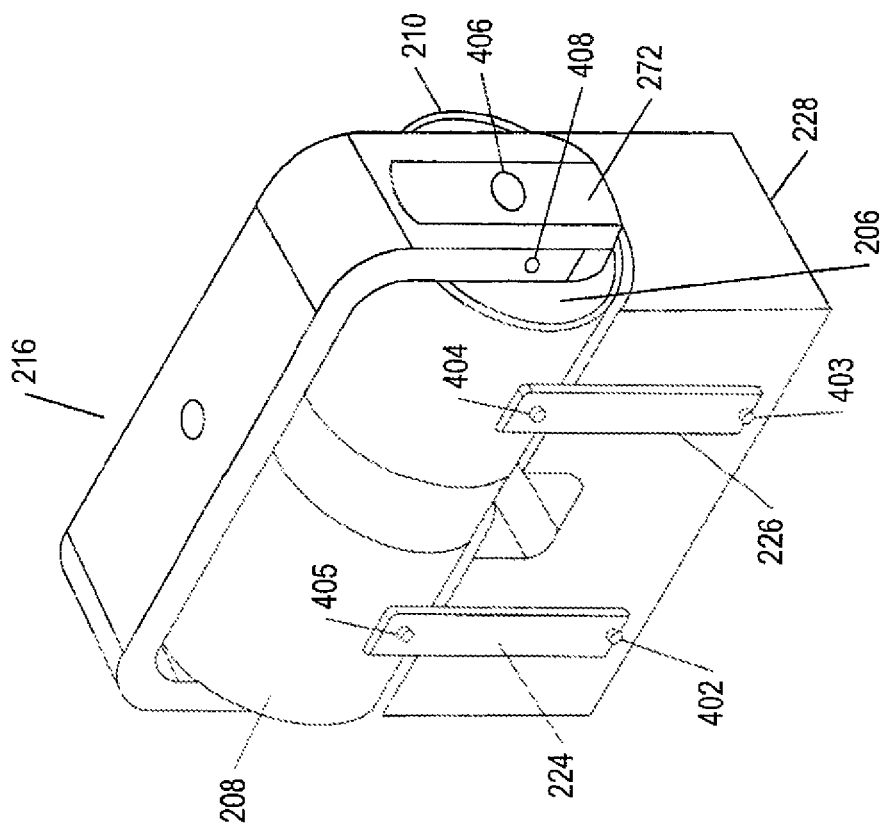
FIG. 4 shows the assembled two-way, by-passable overrunning clutch mechanism of the currently disclosed prosthetic knee.

FIG. 4 shows the assembled two-way, by-passable overrunning clutch mechanism of the currently disclosed prosthetic knee. In this view, the yoke 216 is securely mounted over the vertical bars 272 of the arbors 206, only one of which is visible in FIG. 4. The two flexible linkages 224 and 226 are shown mounted to the lower-leg block 228 and the arbor sleeves 208 and 210 via pins 402-405. The end of clutch pin 214, 408, is seen at the edge of the yoke 216 and the end 406 of the cam-like force adjustor and dimensional constraint 218 in FIG. 2 is seen on the outer surface of the vertical bar 272 of the arbor 206.

Figure 5:
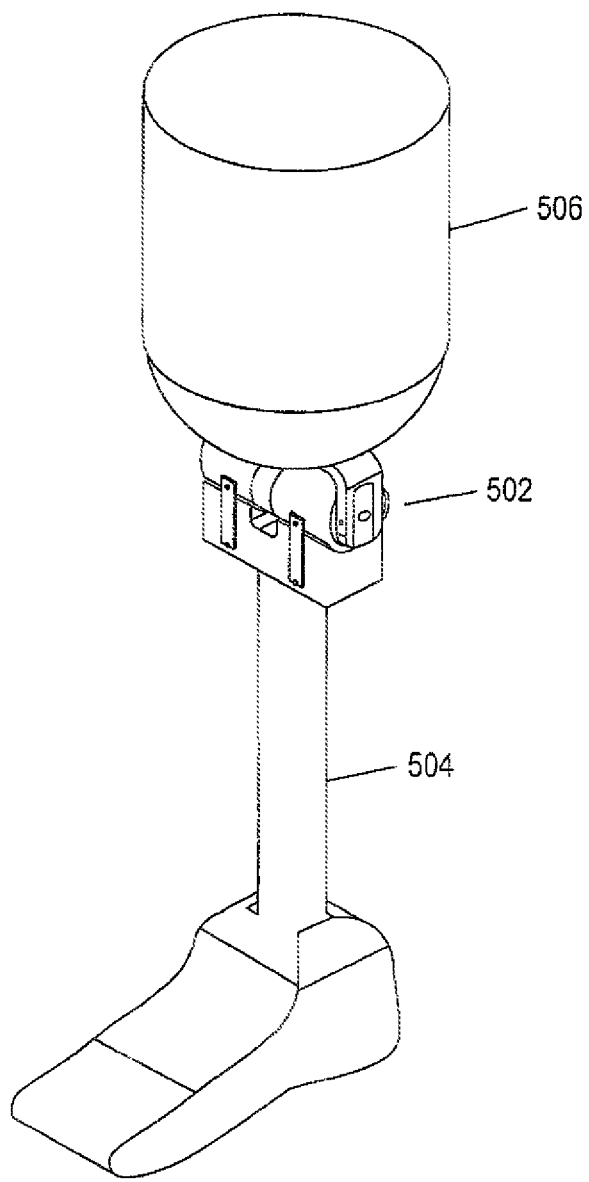
FIG. 5 shows a prosthetic leg that incorporates the two-way, by-passable overrunning clutch described above.
Figure 6A:
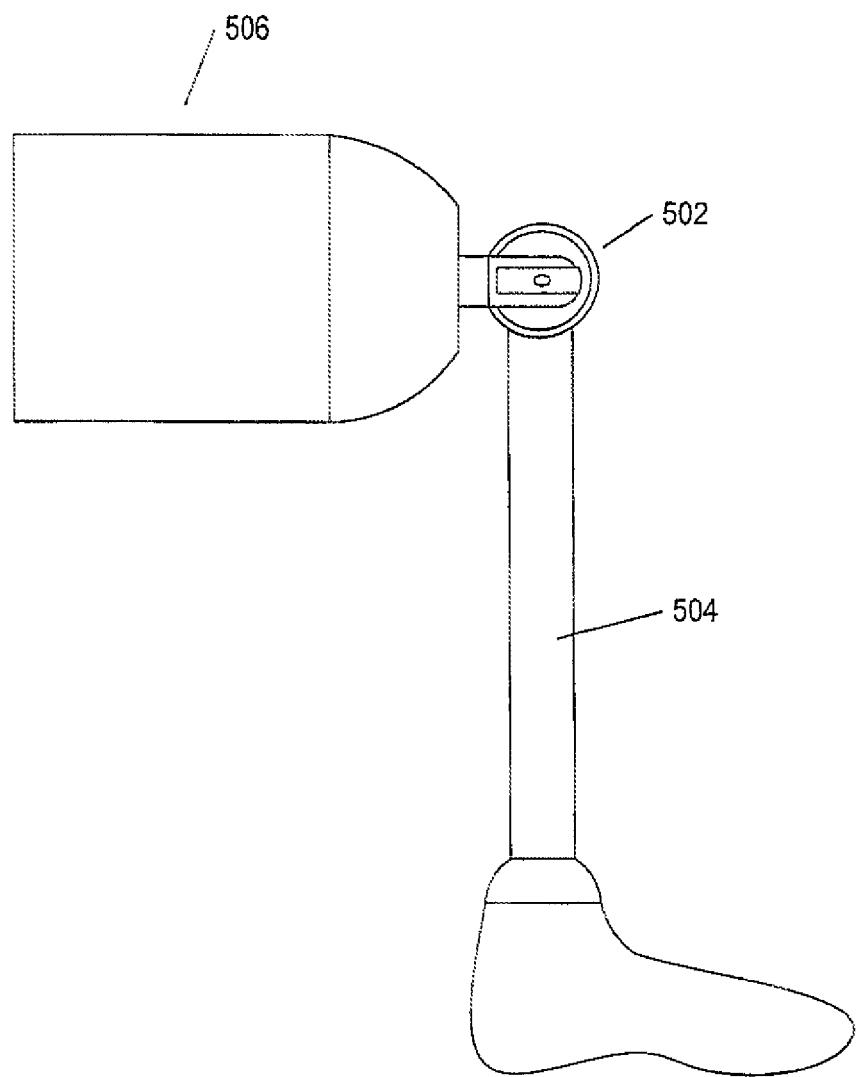
FIGS. 6A-C illustrate operation of the prosthetic leg shown in FIG. 5.
Figure 6B:
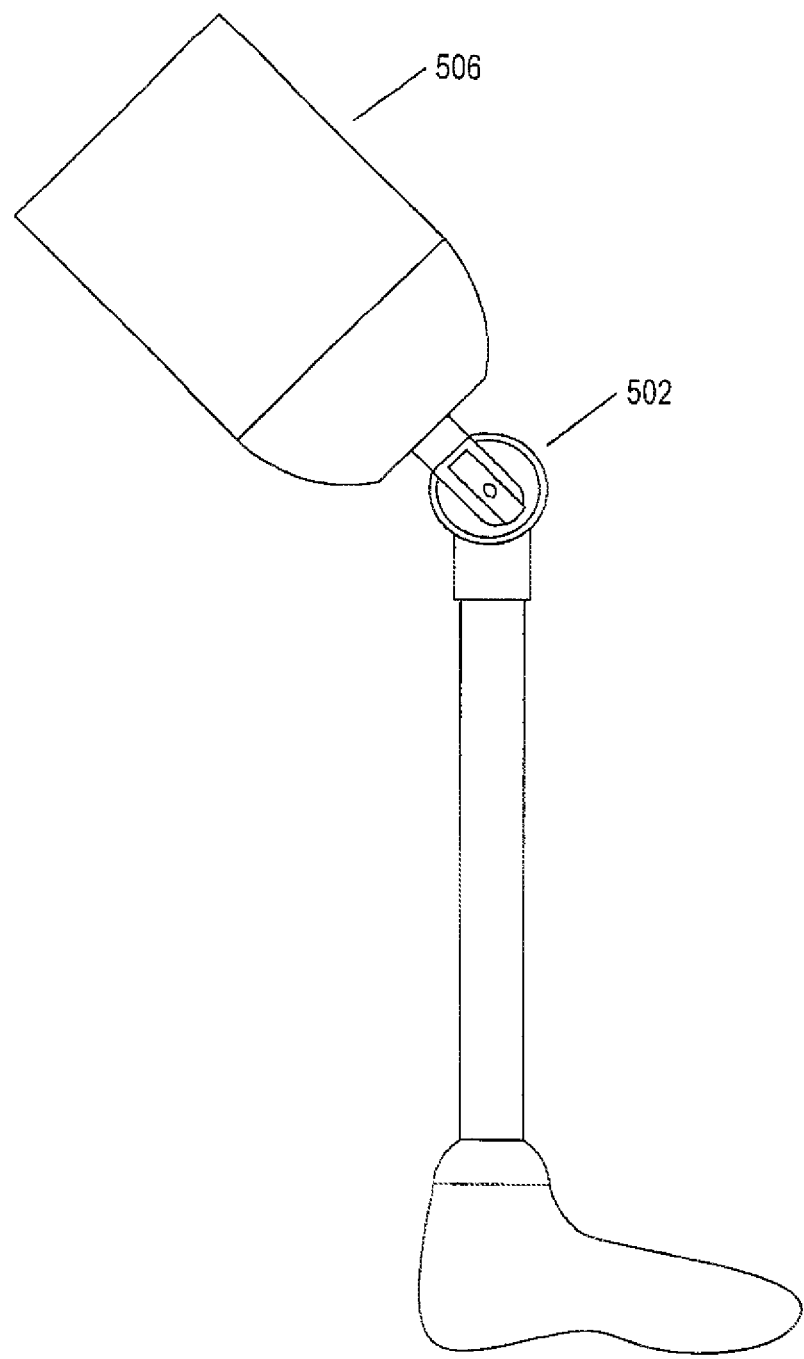
Figure 6C:
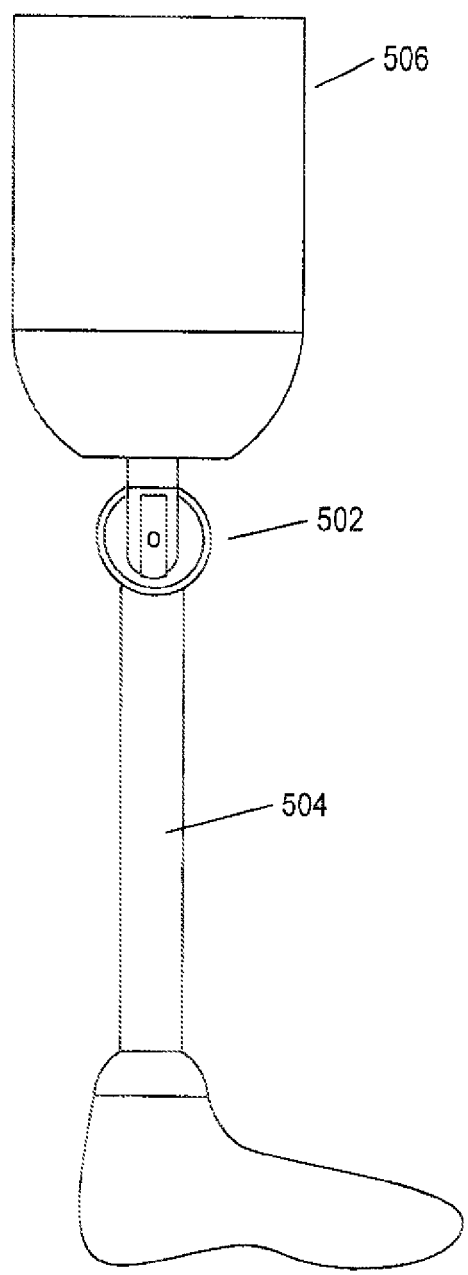

FIG. 5 shows a prosthetic leg that incorporates the two-way, by-passable overrunning clutch described above. The two-way, by-passable overrunning mechanical clutch 502 is shown attached to a lower-leg shank 504 and to an upper-leg truncated-limb sleeve 506. FIGS. 6A-C illustrate operation of the prosthetic leg shown in FIG. 5. When the amputee is sitting, the truncated-limb sleeve 506 is orientated approximately orthogonally to the lower-leg shaft 504. The two-way, by-passable overrunning clutch mechanism 502 is unweighted, and thus the clutch mechanism is disabled. As shown in FIG. 6B, as the amputee begins to stand, the two-way, by-passable overrunning clutch 502 is partially weighted, resulting in an enabling of the clutch and resistance to rotation of the truncated-limb sleeve 506 back downward to the position shown in FIG. 6A. In FIG. 6C, the amputee is standing on the prosthetic limb, as a result of which the two-way, by-passable overrunning clutch 502 is enabled, preventing rotation of the truncated-limb sleeve 506 backward with respect to the lower-leg shank 504 but allowing free rotation of the lower-leg shank 504 in a counter clockwise direction relative to the truncated-limb sleeve 506.

Figure 7:
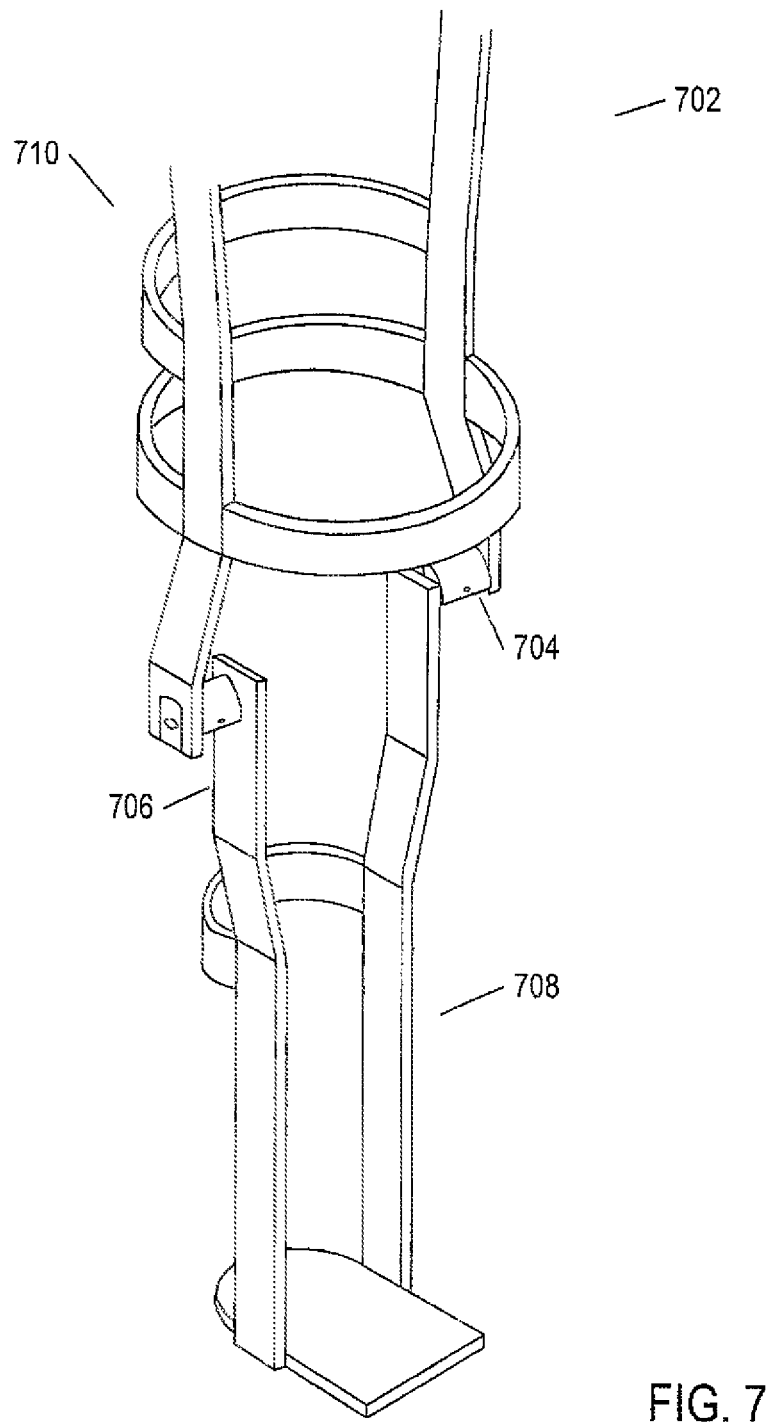
FIG. 7 shows an orthotic exoskeleton-like device that may be worn to promote healing of an injured leg or to provide increased functionality to a damaged limb.

FIG. 7 shows an orthotic exoskeleton-like device that may be worn to promote healing of an injured leg or to provide increased functionality to a damaged limb. The orthotic 702 incorporates several two-way, by-passable overrunning mechanical clutch mechanisms 704 and 706 to provide for free rotation of the lower-leg portion of the orthotic 708 with respect to the upper portion of the orthotic 710 when the orthotic is unweighted but preventing rotation of the lower-leg portion 708 backward, in a clockwise direction, with respect to the upper-leg portion 710 when the orthotic is weighted.

Figure 8A:
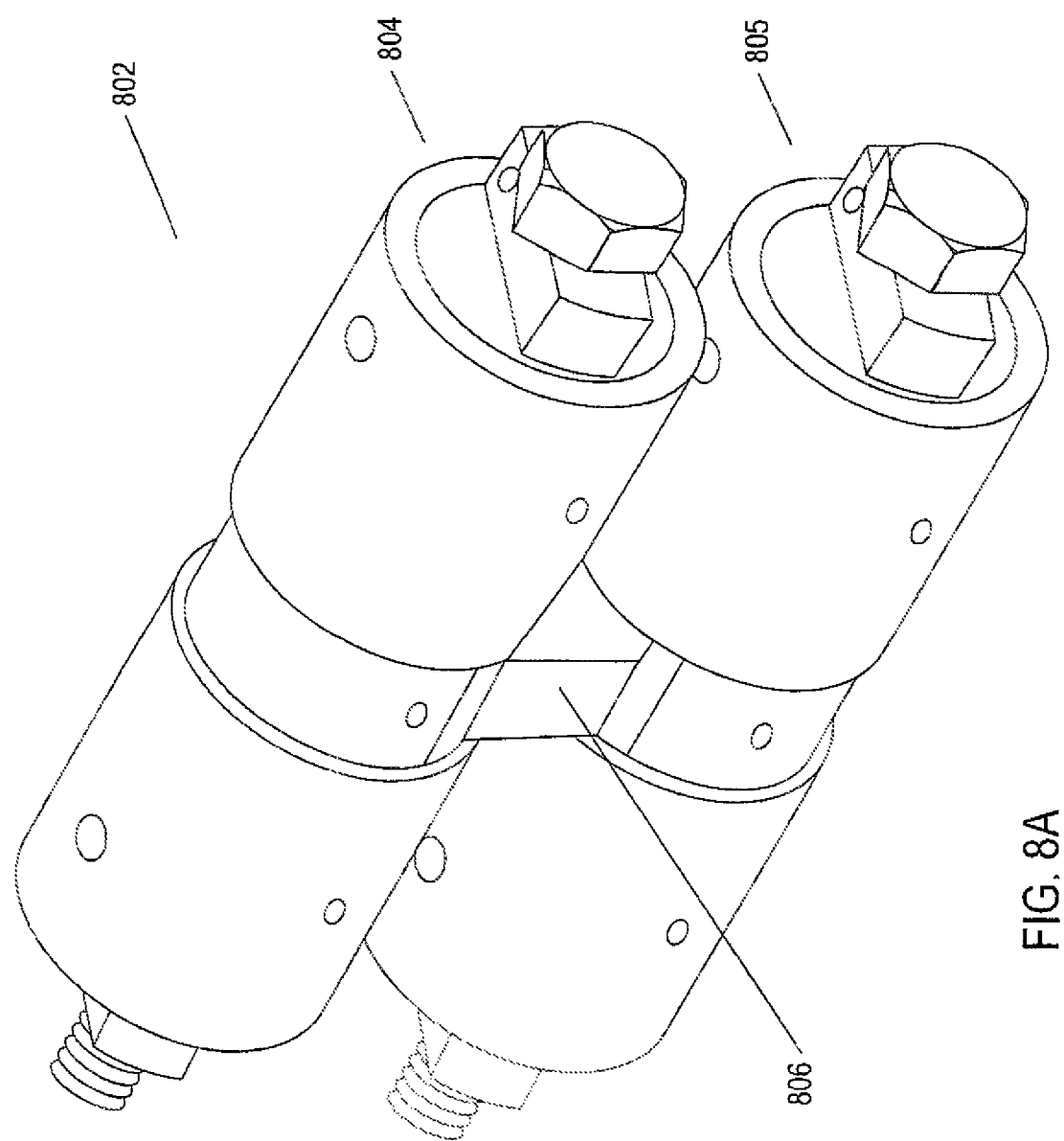
FIGS. 8A-B illustrate dual-mechanical-clutch assemblies that may be incorporated into more complex prosthetic joints and robot assemblies.
Figure 8B:
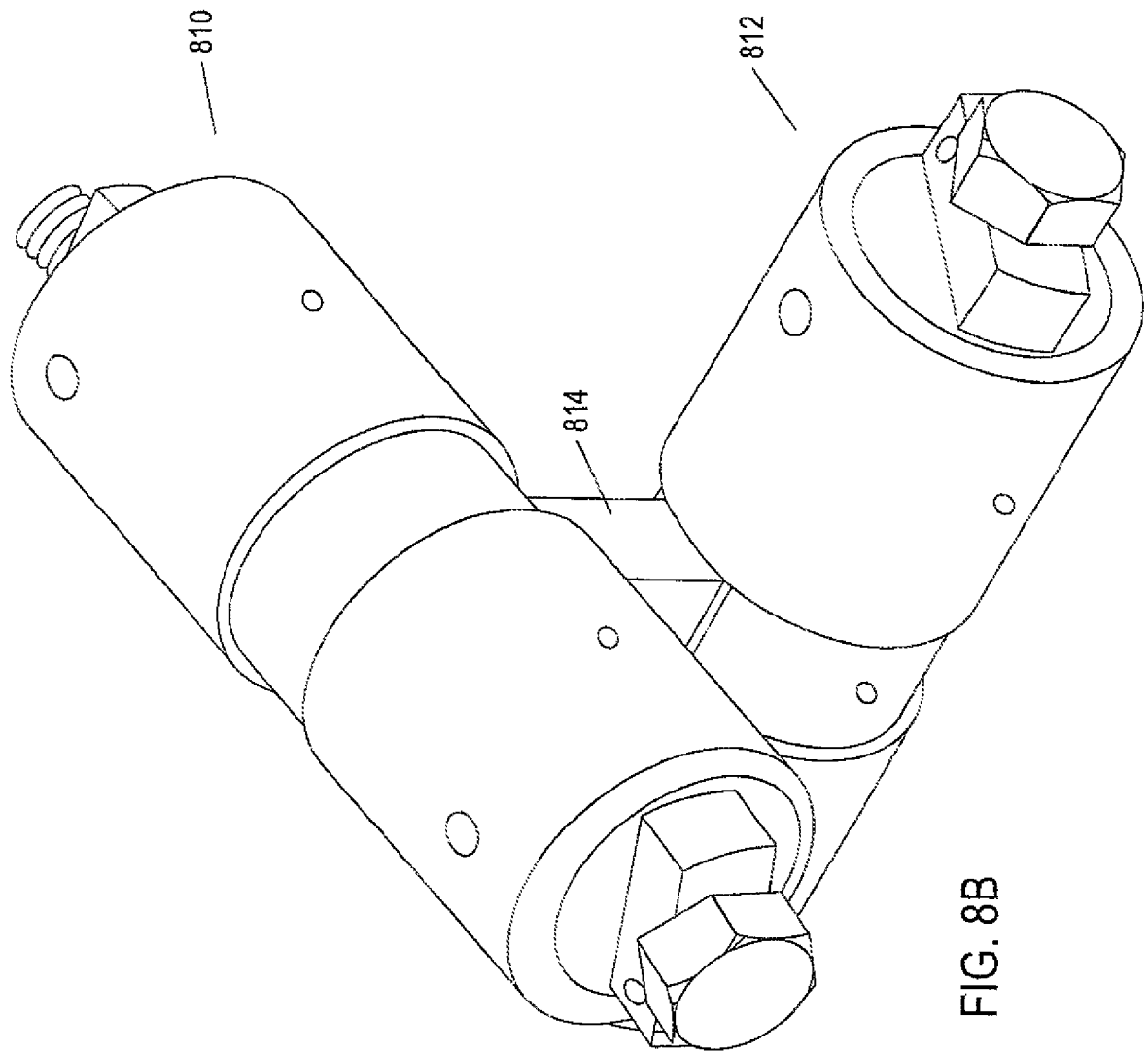

FIGS. 8A-B illustrate dual-mechanical-clutch assemblies that may be incorporated into more complex prosthetic joints and robot assemblies. In the dual-mechanical-clutch assembly shown in FIG. 8A 802, two two-way, by-passable overrunning clutch mechanisms 804-805 are joined together by a fixed member 806 joined to, or incorporating, the central bands of the two WSCs within the two two-way, by-passable mechanical clutch mechanisms 804-805. FIG. 8B shows an alternative dual-clutch mechanism in which the two two-way, by-passable overrunning clutch mechanisms 810 and 812 are orthogonally disposed to one another through connecting member 814.

Although the present invention has been described in terms of particular embodiments, it is not intended that the invention be limited to these embodiments. Modifications within the spirit of the invention will be apparent to those skilled in the art. For example, the various components of the two-way, by-passable overrunning clutch mechanism may be made from a variety of different materials, including metals, composites, plastics, and other materials. They may be molded, cast, machined, or even printed by 3D printing. The flexible links, described above, may be flexible and fixed at either end, as described, or may alternatively be rigid and pivot about their attachment points. The interface between the WSC central body and the shank may be of any form that resists or prevents relative rotation between the two but allows relative longitudinal translation. Examples include but are not limited to a Sarrus linkage, multiple linear shafts, shafts of different cross-section, or a flexible beam. The control methodology may be inverted, with upper leg movement relative to the WSC controlling the braking action of the WSC. Control sleeves may be rotated by mechanical means as previously described, or by induced electromagnetic fields, pneumatic systems, or hydraulic systems. Pneumatic, hydraulic, or electromagnetic systems could provide the adjustable spring force between the WSC and shank. The non-microprocessor mechanical prosthetic knee joint may be coupled with additional WSC units of the same or similar type to create a joint system that has multiple axes of rotation (e.g., polycentric knees) as in FIG. 6A. Further, the axes of rotation may lie in any arbitrary plane(s), thus providing motion in different directions (e.g., shoulder joint, hip joints, etc.). The currently disclosed two-way, by-passable, overrunning clutch may be used as a joint in the limb(s) of a robot. In particular, the knee joint system enables a walking robot to walk more efficiently, with greater stability, and with increased ability to recover from falls. The non-microprocessor mechanical prosthetic knee joint can be split into two parts through the WSC central body. This enables mounting of the joint system on either side of an intact knee or other joint, to serve as an integral component of an exoskeleton or orthotic system. In such case a user need not be an amputee, but instead may use the non-microprocessor mechanical prosthetic knee joint to augment or supplement their existing strength, gait, posture, and/or range of motion. As mentioned above, the two-way, by-passable overrunning clutch mechanism may additionally be incorporated in a variety of electromechanical and higher-end prosthetics.

It is appreciated that the previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

The invention claimed is:

1. A mechanical joint comprising:
   a lower-leg block;
   a yoke assembly; and
   a friction-based clutch-element member of the yoke assembly that mechanically prevents rotation of the lower-leg block relative to the yoke assembly in one rotational direction when the mechanical joint is weighted, which forces a coil against a cylindrical surface to generate friction that prevents rotation of the lower-leg block relative to the yoke assembly in the one rotational direction, and that mechanically permits free rotation of the lower-leg block relative to the yoke assembly when the mechanical joint is unweighted, which releases the coil from the cylindrical surface.

2. The mechanical joint of claim 1 wherein the yoke assembly further comprises:
   a yoke-arbor subassembly that includes a yoke with a first arbor mount and a second arbor mount;
   a first arbor with a cylindrical shaft mounted to the first arbor mount;
   a second arbor with a cylindrical shaft mounted to the second arbor mount; and
   the clutch element having
      a central cylindrical band,
      a first coil attached to a first edge of the central cylindrical band and spiraling away from the central cylindrical band, the first coil rotatably mounted to the first arbor; and a second coil attached to a second edge of the central cylindrical band and spiraling away from the central cylindrical band in a direction opposite from that of the first coil, the second coil rotatably mounted to the second arbor.

3. The mechanical joint of claim 2 wherein the first and second coils clamp down on the cylindrical surfaces of the first and second cylindrical shafts of the first and second arbors, respectively, when the mechanical joint is weighted to prevent rotation of the lower-leg block relative to the yoke assembly in the one rotational direction.

4. The mechanical joint of claim 2
   wherein the yoke includes a structural member, the first arbor mount, and the second arbor mount;
   wherein each of the first and second arbors includes mounting members complementary to the first arbor mount and the second arbor mount, respectively;
   wherein, when the mounting member of the first arbor is fitted to the first arbor mount and is additionally secured to the first arbor mount by a first securing member, the first arbor is rigidly mounted to the yoke; and
   wherein, when the mounting member of the second arbor is fitted to the second arbor mount and is additionally secured to the second arbor mount by a second securing member, the second arbor is rigidly mounted to the yoke.

5. The mechanical joint of claim 2 wherein the yoke assembly further comprises:
   a first cylindrical arbor sleeve that is rotatably mounted to the cylindrical shaft of the first arbor, with the first coil lying between an inner surface of the first cylindrical arbor sleeve and a surface of the cylindrical shaft, an end member of the first coil mated to a complementary member of the first cylindrical arbor sleeve; and
   a second cylindrical arbor sleeve that is rotatably mounted to the cylindrical shaft of the second arbor, with the second coil lying between an inner surface of the second cylindrical arbor sleeve and a surface of the cylindrical shaft, an end member of the second coil mated to a complementary member of the second cylindrical arbor sleeve.

6. The mechanical joint of claim 5 wherein, when the mechanical joint is unweighted, the first and second cylindrical arbor sleeves are rotated with respect to the first and second arbors, respectively, imparting a twisting force to the first and second coils, respectively, which results in loosening the interaction between the coils and the cylindrical surfaces of the arbor shafts, allowing free rotation of the lower-leg block with respect to the yoke assembly.

7. The mechanical joint of claim 5 wherein linking members that link the lower-leg block to the cylindrical arbor sleeves provide a rotational force to the cylindrical arbor sleeves when the lower-leg block moves away from the clutch element.

8. The mechanical joint of claim 5 wherein the end members of the first and second coils are cross sections of a regular prism that fit into the complementary members of the first and second cylindrical arbor sleeve.

9. The mechanical joint of claim 5
wherein a torque-transmission pin is spring mounted to the lower-leg block and passes through an aperture in the central cylindrical band; and
wherein the yoke assembly further comprises a cylindrical cam that includes a partial shaft aperture within which the torque-transmission pin slides.

10. The mechanical joint of claim 9 wherein the torque-transmission pin rotationally couples the lower-leg block to the clutch element.

11. The mechanical joint of claim 9 wherein the cylindrical cam is secured to the yoke so that the depth of shaft aperture varies as the torque-transmission pin and lower-leg block rotate with respect to the yoke assembly.

12. The mechanical joint of claim 1
wherein the lower-leg block is rigidly affixed to a lower prosthetic leg; and
wherein the yoke assembly is rigidly affixed to an upper prosthetic leg.

13. The mechanical joint of claim 12 wherein the mechanical joint mechanically permits the upper prosthetic leg to freely rotate relative to the lower prosthetic leg when the upper prosthetic is unweighted as it is swung forward during the swing phase of a gait cycle.

14. The mechanical joint of claim 12 wherein the mechanical joint mechanically permits the upper prosthetic leg to rotate relative to the lower prosthetic leg when the upper prosthetic leg rotates with respect to the lower prosthetic leg during a transition from sitting to standing and during a transition from standing to sitting despite partial weighting of the upper prosthetic leg.

15. The mechanical joint of claim 12 wherein the mechanical joint mechanically prevents the upper prosthetic leg from rotating relative to the lower prosthetic leg, as it would during a transition from standing to sitting, during the stance phase of a gait cycle.

\* \* \* \* \*